United States Patent [19]

Oka et al.

[11] Patent Number: 5,688,643
[45] Date of Patent: Nov. 18, 1997

[54] METHOD OF NUCLEIC ACID-DIFFERENTIATION AND ASSAY KIT FOR NUCLEIC ACID DIFFERENTIATION

[75] Inventors: Takanori Oka; Hironari Matsunaga; Akio Yamane, all of Hiroshima, Japan

[73] Assignee: Wakunaga Seiyaku Kabushiki Kaisha, Osaka, Japan

[21] Appl. No.: 392,818

[22] PCT Filed: Jul. 7, 1994

[86] PCT No.: PCT/JP94/01106

§ 371 Date: Feb. 27, 1995

§ 102(e) Date: Feb. 27, 1995

[87] PCT Pub. No.: WO95/02068

PCT Pub. Date: Jan. 19, 1995

[30] Foreign Application Priority Data

Jul. 9, 1993 [JP] Japan .................................. 5-194196

[51] Int. Cl.[6] .............................. C12Q 1/68; C12N 15/00
[52] U.S. Cl. .................................. 435/6; 935/77; 935/78
[58] Field of Search ........................................ 435/6

[56] References Cited

U.S. PATENT DOCUMENTS

| 4,605,735 | 8/1986 | Miyoshi et al. |
| 4,667,025 | 5/1987 | Miyoshi et al. |
| 4,789,737 | 12/1988 | Miyoshi et al. |
| 4,849,336 | 7/1989 | Miyoshi et al. |

FOREIGN PATENT DOCUMENTS

| 0362042 | 4/1990 | European Pat. Off. |
| WO89/06285 | 7/1989 | WIPO |

OTHER PUBLICATIONS

Conner et al, Proc. Natl. Acad. Sci. USA, vol. 80, pp. 278–282 (Jan. 1983).

Kohonen–Corish et al, Am. J. Human Genetics, vol. 39, pp. 751–762 (1986).

Myers et al, Science, vol. 230, pp. 1242–1246 (Dec. 13, 1985).

Sarkar et al, Analytical Biochemistry, vol. 186, pp. 64–68 (1990).

Térouanne et al, Analytical Biochemistry, vol. 205, pp. 193–199 (1992).

Barany, Proc. Natl. Acad. Sci. USA, vol. 88, pp. 189–193 (Jan. 1991).

Sheffield et al, Proc. Natl. Acad. Sci. USA, vol. 86, pp. 232–236 (Jan. 1989).

Orita et al, Proc. Natl. Acad. Sci. USA, vol. 86, pp. 2766–2770 (Apr. 1989).

(List continued on next page.)

*Primary Examiner*—W. Gary Jones
*Assistant Examiner*—Ethan Whisenant
*Attorney, Agent, or Firm*—Birch, Stewart, Kolasch & Birch, LLP

[57] ABSTRACT

A nucleic acid differentiating method is provided which involves using a primer having a detectable label introduced therein and a primer having a solid matrix-binding site introduced therein, amplifying a particular region of a target nucleic acid in a sample to thereby produce a labeled sample DNA, adding to this labeled sample DNA at least an equimolar amount of an unlabeled standard DNA to be evaluated for its sequence matching with the sample DNA, effecting competitive hybridization, and at the end of reaction, determining the label intensity of the hybridization product, for thereby determining the presence/absence of a mutant gene in the nucleic acid, the ratio of normal to mutant genes, or the sequence matching of a particular gene among a plurality of samples.

An assay kit for differentiating nucleic acid by the differentiating method is also provided which includes target nucleic acid-amplifying primers comprising a primer having a detectable label introduced therein and a primer having a solid matrix-binding site introduced therein and an unlabeled DNA specimen to be evaluated for its matching with the amplified product amplified with the primers.

9 Claims, 4 Drawing Sheets

OTHER PUBLICATIONS

Ubukata et al, Journal of Clinical Microbiology, vol. 30, No. 7, pp. 1728–1733 (Jul. 1992).

PCR Protocols, Academic Press Inc., pp. 14–15 and 352–353 (1990).

PCR Technology, Henry A. Erlich, Ed., Stockton Press (1989) (Introductory pages only).

Saiki et al, Nature, vol. 324, pp. 163–168 (Nov. 1986).

Maeda et al, Tissue Antigens, vol. 34, pp. 290–298 (1989).

Olerup et al, Tissue Antigens, vol. 39, pp. 225–235 (1992).

Jikken Igaku, Experimental Medicine, Yohdo–sha, vol. 8, No. 9 (1990).

Sekiya et al, Gann, vol. 74, pp. 794–797 (Dec. 1983).

Yuasa et al, Nature, vol. 303, pp. 775–779 (Jun. 30, 1983).

Ho et al, Gene, vol. 77, pp. 51–59 (1989).

The Stratagene Catalog p. 39 (1988).

Terouanne et al, Analytical Biochemistry, 205, 193–199 (1992).

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="primer"

( i i i ) HYPOTHETICAL: NO ( i v ) ANTI-SENSE: NO ( v i ) ORIGINAL SOURCE:
( A ) ORGANISM: Homo sapiens ( x i ) SEQUENCE DESCRIPTION: SEQ ID NO:1:

GGGTTGGCCA ATCTACTCCC AG 22

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
    ( A ) DESCRIPTION: /desc ="PRIMER"

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:2:

CAACTTCATC CACGTTCACC　　　　　　　　　　　　　　　　　　　　　　　　20

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:3:

ATGACGGAAT ATAAGCTGGT G　　　　　　　　　　　　　　　　　　　　　　　21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:4:

CTCTATAGTG GGGTCGTATT C　　　　　　　　　　　　　　　　　　　　　　　21

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:5:

ATTGTGAGGA CACTGCTCCT ACACCCAGCC 30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:6:

TACGATACAG AATATATGTG CCATGGGGCC 30

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:7:

GATTTATAAG AAGTAATAC TTCCTTGCAC AG 32

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:8:

AAGTATTAAC TTCTTATAAA TCAAACT 27

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single (D) TOPOLOGY: linear (ii) MOLECULE TYPE: other nucleic acid
  (A) DESCRIPTION: /desc ="PRIMER"

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:9:

GATTATGGGA GAACTGGAGC CTTCAGAGGG     30

(2) INFORMATION FOR SEQ ID NO:10:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc ="PRIMER"

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:10:

CTTCTAGTTG GCATGCTTTG ATGACGCTTC     30

(2) INFORMATION FOR SEQ ID NO:11:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc ="PRIMER"

(iii) HYPOTHETICAL: NO (iv) ANTI-SENSE: NO (vi) ORIGINAL SOURCE:
  (A) ORGANISM: Homo sapiens (xi) SEQUENCE DESCRIPTION: SEQ ID NO:11:

AAATATCATC GGTGTTTCCT ATGA     24

(2) INFORMATION FOR SEQ ID NO:12:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc ="PRIMER"

(iii) HYPOTHETICAL: NO (iv) ANTI-SENSE: NO (vi) ORIGINAL SOURCE:
  (A) ORGANISM: Homo sapiens ( x i ) SEQUENCE DESCRIPTION: SEQ ID NO:12:

CACCGATGAT ATTTTCTTTA ATG    23

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:13:

GAAGGAAGAT GTGCCTTTCA AATTCAGATT G    31

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:14:

ATGACATTTA CAGCAAATGC TTGCTAGACC    30

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:15:

CACTGAGTGG AGATCAACGA GCAAGAATTT CT    32

( 2 ) INFORMATION FOR SEQ ID NO:16:

( i ) SEQUENCE CHARACTERISTICS:
        ( A ) LENGTH: 28 base pairs
        ( B ) TYPE: nucleic acid ( C ) STRANDEDNESS: single
           ( D ) TOPOLOGY: linear ( i i ) MOLECULE TYPE: other nucleic acid
           ( A ) DESCRIPTION: /desc ="PRIMER"

( i i i ) HYPOTHETICAL: NO ( i v ) ANTI-SENSE: NO ( v i ) ORIGINAL SOURCE:
           ( A ) ORGANISM: Homo sapiens ( x i ) SEQUENCE DESCRIPTION: SEQ ID NO:16:

GCTCGTTGAT CTCCACTCAG TGTGATTC                                          2 8

( 2 ) INFORMATION FOR SEQ ID NO:17:

( i ) SEQUENCE CHARACTERISTICS:
           ( A ) LENGTH: 30 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc ="PRIMER"

( i i i ) HYPOTHETICAL: NO ( i v ) ANTI-SENSE: NO ( v i ) ORIGINAL SOURCE:
           ( A ) ORGANISM: Homo sapiens ( x i ) SEQUENCE DESCRIPTION: SEQ ID NO:17:

AGAGAACTTG ATGGTAAGTA CATGGGTGTT                                        3 0

( 2 ) INFORMATION FOR SEQ ID NO:18:

( i ) SEQUENCE CHARACTERISTICS:
           ( A ) LENGTH: 30 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc ="PRIMER"

( i i i ) HYPOTHETICAL: NO ( i v ) ANTI-SENSE: NO ( v i ) ORIGINAL SOURCE:
           ( A ) ORGANISM: Homo sapiens ( x i ) SEQUENCE DESCRIPTION: SEQ ID NO:18:

TTAGCAGCCT TACCTCATCT GCAACTTTCC                                        3 0

( 2 ) INFORMATION FOR SEQ ID NO:19:

( i ) SEQUENCE CHARACTERISTICS:
           ( A ) LENGTH: 31 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc ="PRIMER"

( i i i ) HYPOTHETICAL: NO ( i v ) ANTI-SENSE: NO ( v i ) ORIGINAL SOURCE:

( A ) ORGANISM: Homo sapiens ( x i ) SEQUENCE DESCRIPTION: SEQ ID NO:19:

CATTTAGAAA AAAGTTGGAT CCCTATGAAC A        31

( 2 ) INFORMATION FOR SEQ ID NO:20:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="PRIMER"

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:20:

GGGATCCAAC TTTTTCTAA ATGTTCCAG        29

( 2 ) INFORMATION FOR SEQ ID NO:21:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="PRIMER"

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:21:

GATCAGGCCT AAAAGGCCT        19

( 2 ) INFORMATION FOR SEQ ID NO:22:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: other nucleic acid
            ( A ) DESCRIPTION: /desc ="PRIMER"

( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:22:

GATCAGGCCT TTTAGGCCT        19

( 2 ) INFORMATION FOR SEQ ID NO:23:

( i ) SEQUENCE CHARACTERISTICS:
            ( A ) LENGTH: 36 base pairs ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:23:

TTTAGGCCTA AAAGGCCTGA TTATGGGAGA ACTGGA         36

( 2 ) INFORMATION FOR SEQ ID NO:24:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:24:

CCCAGGCCTT TTAGGCCTCT TCTAGTTGGC ATGCTT         36

METHOD OF NUCLEIC ACID-DIFFERENTIATION AND ASSAY KIT FOR NUCLEIC ACID DIFFERENTIATION

TECHNICAL FIELD

This invention relates to a method for differentiating a nucleic acid and an assay kit for such nucleic acid-differentiation. More specifically, this invention relates to a nucleic acid differentiating method that is capable of directly and quickly evaluating a specimen for the presence/absence of a mutant gene in a nucleic acid as well as the ratio of mutant to normal genes and that enables various assays that have been difficult to accomplish by conventional methods, for example, detection of a mutation at a non-specific site within a gene, detection of a small amount of abnormal cells containing a mutant gene in a mixture with normal cells, and determination of sequence matching of a particular gene in a plurality of samples; and an assay kit which may be used for nucleic acid-differentiation by the same method.

BACKGROUND ART

Molecular biology and genetics have experienced a marked progress in recent years, and the findings accumulated in such fields would contribute not only to chemical/physical clarification of various phyenomena involved in life, but also to human lives, in particular, to medicine as a field and a practice. DNA medicine starting from DNA is expanding to a clinical field far beyond expectation. It is known today that almost all diseases are related to DNA, and a diagnosis on a genetic level has become indispensable.

It is now recognized that nearly all enzyme deficiencies that are known for many years as inborn errors of metabolism are ascribed to diseases that are generally referred to as genetic diseases (molecular diseases). Detection of a mutation in a gene is quite effective for the diagnosis of such genetic diseases.

Typical conventional methods for detecting a mutation in a gene that can be used when the site of the genetic mutation is already known include a detection method using an oligonucleotide probe (PNAS, 80, 278, 1983): a method utilizing restriction enzyme polymorphism (Am. J. Hum. Genet., 69, 201, 1980); and scission of a one-base mismatch in a RNA:DNA hybrid by utilizing ribonuclease (Science, 230, 1243, 1985).

Mutation detection utilizing gene amplification was also developed (Proc. Natl. Acad. Sci. USA, 88, 189, 1991); Anal. Biochem, 186, 64–68, 1990). These methods, however, can be used only when the base sequence has already been found out and are limited to the detection of a specific mutation. On the other hand, SSCP method (Proc. Natl. Acad. Sci. USA, 86, 2766, 1989), DGGE method (Proc. Natl. Acad. Sci. USA, 86, 232, 1989), and other methods were reported as methods for detecting a non-specific mutation (site and base) in a certain region. These methods, however, use electrophoresis and are not necessarily practical when the ease and quickness of operation are taken into account.

Then J. C. Nicolas developed the following method as a system for detecting a non-specific mutation within a certain region of a nucleic acid (EP-A 362042 and Terouanne et al. Anal. Biochem., 205, 193, 1992). First a biotin label is introduced into one of duplex strands in a nucleic acid fragment containing a region to be detected for mutation, and an FITC label is introduced into the other strand to thereby produce a labeled standard DNA. The labeled standard DNA is mixed with an excessive amount of a sample DNA containing an unlabeled nucleic acid fragment of the same region as the standard DNA. The mixture is heated for denaturing and then slowly cooled down (competitive hybridization). When a fragment with a base sequence in complete conformity with that of the labeled standard DNA is present in the sample, recombination of double stranded DNA occurs between the duplex strands of the labeled standard DNA and the duplex strands of the sample DNA, whereupon the amount of the labeled standard DNA having both the biotin label and the FITC label that has been initially present is reduced. On the other hand, when a fragment with a base sequence partly different from that of the labeled standard DNA is present in the sample, the aforementioned recombination between the duplex strands of the labeled standard DNA and the duplex strands of the sample DNA is less likely to occur so that the amount of the labeled standard DNA that has been initially present remains substantially unchanged. Namely, this method is to judge whether or not a fragment containing the same base sequence as that of the labeled standard DNA is present, by observing a change from the initially added amount of the labeled standard DNA after the (competitive hybridization) procedure of mixing, denaturing, and annealing.

In general, congenital hereditary diseases include dominantly transmitting diseases and recessively transmitting diseases. The former will express their phenotype even when genetic abnormality is present only in one of alleles (heteroallelic), while the latter will express their phenotype only when genetic abnormality is present in both alleles (homoallelic). In the case of recessive heredity, the genetic abnormality would not manifest as a disease when the genetic abnormality is present only on one of alleles, but with a fair chance that the descendant will inherit such genetic abnormality. Therefore, examination of genetic abnormality is of great significance irrespective of homo/hetero. Furthermore, in the typing of human leukocyte antigen (HLA), even if the alleles in a sample are determined to be homoallelic, a prior art method is impossible to accurately confirm whether they are really homoallelic. There is a demand to establish such a confirmation method.

Still further, in carrying out genetic diagnosis of diseases such as cancer that are caused by acquired gene abnormality, it is quite difficult to collect only cancer cells from a cancer lesion, and normal cells are always mixed therewith. If a mutant gene in mutant cells can be detected under a situation where mutant cells are present in admixture with normal cells, it is of great significance in the diagnosis of acquired genetic diseases such as cancer.

However, using the method of Nicolas referred to above it is difficult to accurately detect mutant gene in a situation where the mutant gene is present in admixture with a normal gene. For example, when a nucleic acid fragment containing a normal gene is used as the labeled standard DNA, the resulting signals would not exhibit a significant difference between the case wherein one-half of the genes in the sample nucleic acid are normal (heteroallelic) and the case wherein all the genes in the sample are normal (normal and homoallelic). Therefore, these methods are insufficient for diagnosing the diseases associated with gene abnormality.

Therefore, there is a desired to have a nucleic acid differentiation technique that is effective and practical for the diagnosis of a hereditary disease or the like.

DISCLOSURE OF THE INVENTION

An object of the present invention is to provide a nucleic acid differentiation method which is capable of detecting the presence or absence of non-specific mutation in a particular region of a gene as well as whether such mutation has occurred on both or either one of alleles, which is capable of detecting a slight amount of mutant cells in a mixture with normal cells and determining the ratio of mutant to normal cells, and which is capable of confirming whether the specific alleles are in complete conformity among a plurality of specimens; and an assay kit for differentiating a nucleic acid that is used in the practice of the nucleic acid differentiation method.

In order to attain the above objects, the inventors carried out the following experiments by utilizing a target nucleic acid-detection system using a target nucleic acid comprising a primer having a detectable label introduced therein and a primer having a solid matrix-binding site introduced therein (ED-PCR method; see Japanese Patent Application Laid-Open (JP-A) Nos. 1-314965 and 1-252300, Ubukata et al., J. Clin. Microbiol. 30, 1728, 1992, for example) while making an intensive study thereabout.

First a sample DNA which is expected to contain a mutant gene was subjected to gene amplification reaction with a pair of the above-mentioned labeled primers, obtaining a labeled sample DNA. Separately a normal gene without such mutation was subjected to gene amplification reaction with a pair of primers having the same base sequence as the labeled primers, but unlabeled, obtaining an unlabeled standard DNA. Next, the labeled sample DNA was mixed with at least an equimolar amount of the unlabeled standard DNA, allowing competitive hybridization to take place. The rate of recombination between the labeled sample DNA and the unlabeled standard DNA was determined by utilizing the ED-PCR system. It was then found that, by adding at least an equimolar amount of the unlabeled standard DNA to the labeled sample DNA, not only the presence or absence of the non-specific mutation within a particular gene region, but also whether such mutation had occurred in both or either one of alleles could be detected, that the mutation could be detected even when the proportion of the mutant gene is as low as about 10%, and that the proportion of the mutant gene could be determined as well. Furthermore, it was found that, if this method is applied for differentiation of specific genes in two sample DNAs by using one DNA as the labeled sample DNA and the other DNA as the unlabeled standard DNA, matching of these genes, that is, whether these genes are identical with each other or whether these genes are completely or partially different from each other, and still further, how these genes are different from each other could be examined. The present invention has been completed based on such findings.

More particularly, the inventors have found that as opposed to the conventional method of mixing a labeled standard DNA with an excessive amount of an unlabeled sample DNA and inducing competitive hybridization, if a labeled sample DNA is mixed with an excessive amount of an unlabeled standard DNA and competitive hybridization is induced, then it becomes possible to detect whether or not mutation has occurred, irrespective of the ratio of mutant to normal genes. It has also been found that there is a linear correlation between the ratio of mutant to normal genes in the specimen and the measurement obtained by quantitating the molecule resulting from competitive hybridization and having both the solid matrix-binding label and the detectable label and that the ratio of mutant to normal genes can be relatively easily calculated from the measurement. Furthermore, it has been found that matching of a particular gene in a plurality of sample DNAs can be examined by using one sample DNA as the labeled sample DNA and another DNA as the unlabeled standard DNA. The present invention has been completed based on such findings.

According to the present invention, there is provided a nucleic acid differentiating method for differentiating a gene in a particular region of a target nucleic acid in a specimen, characterized by comprising the steps of preparing a labeled DNA by effecting gene amplification of the particular region of the target nucleic acid in the specimen by using target nucleic acid-amplifying primers comprising a primer having a detectable label introduced therein and a primer having a solid matrix-binding site introduced therein, using the resulting labeled DNA as a sample DNA, using an unlabeled DNA specimen to be evaluated for it matching with the sample DNA as a standard DNA, adding at least an equimolar amount of said standard DNA to said sample DNA, effecting competitive hybridization, and thereafter measuring a degree of substitution between complementary strands of said sample DNA and said standard DNA by utilizing said detectable label and said solid matrix-binding site, thereby determining the matching between the nucleic acids.

According to the present invention, there is also provided an assay kit for nucleic acid differentiation, characterized by comprising target nucleic acid-amplifying primers comprising a primer having a detectable label introduced therein and a primer having a solid matrix-binding site introduced therein, and an unlabeled DNA specimen to be evaluated for its matching with the gene amplified product amplified by said primers.

The nucleic acid differentiating assay kit of the present invention may be used by mixing the primers for amplifying nucleic acid in the particular region of the target nucleic acid with a specimen, which has been subjected to a pretreatment such as cell disruption treatment if necessary; adding reagents required for nucleic acid amplification to the mixture to effect the amplification of the target nucleic acid in the specimen; adding said unlabeled DNA specimen to the amplified product to effect competitive hybridization; trapping the hybridized DNA on a matrix by utilizing said solid matrix-binding site; and effecting measurement by utilizing the detectable label. In this regard, an assay kit for nucleic acid differentiation is obtained when reagents and materials as used in ED-PCR method, for example, a cell disruption reagent, a reagent for nucleic acid amplification, and a matrix for trapping the hybrid are added to said target nucleic acid-amplifying primers and said unlabeled DNA specimen.

The preferred embodiment of the present invention will be clearly understood by reading the following description.

BEST MODE FOR CARRYING OUT THE INVENTION

The nucleic acid differentiating method of the present invention is constructed such that, as opposed to the conventional method wherein a labeled standard DNA is mixed with an excessive amount of an unlabeled sample DNA to effect competitive hybridization, a labeled sample DNA is mixed with an excess amount of an unlabeled standard DNA to effect competitive hybridization, and a degree of substitution between complementary strands in the sample DNA and the standard DNA is determined, thereby enabling detection of the presence/absence of a non-specific mutation within a particular region of the gene, as well as whether such mutation has occurred on both or either one of the alleles; detection of a slight amount of mutant cells in a mixture with normal cells, as well as the ratio of mutant to normal cells; and confirmation of the matching of the particular alleles among a plurality of samples.

Now the nucleic acid differentiating method of the present invention is theoretically described in comparison with that of Nicolas et al. (the method described in Anal. Biochem., 205, 193, 1992) by referring to the schematic drawings.

Figure 1B:
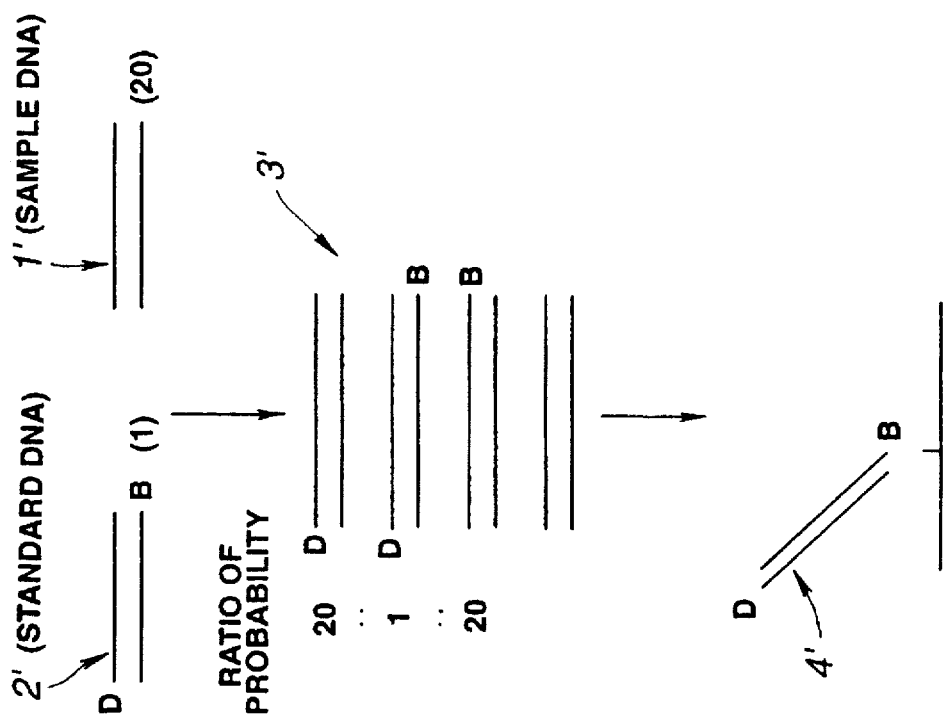
FIGS. 1A and 1B are schematic views illustrating nucleic acid differentiation methods as applied to all normal nucleic acids, FIG. 1A showing the method of the present invention and FIG. 1B showing a prior art method of Nicolas et al.
Figure 1A:
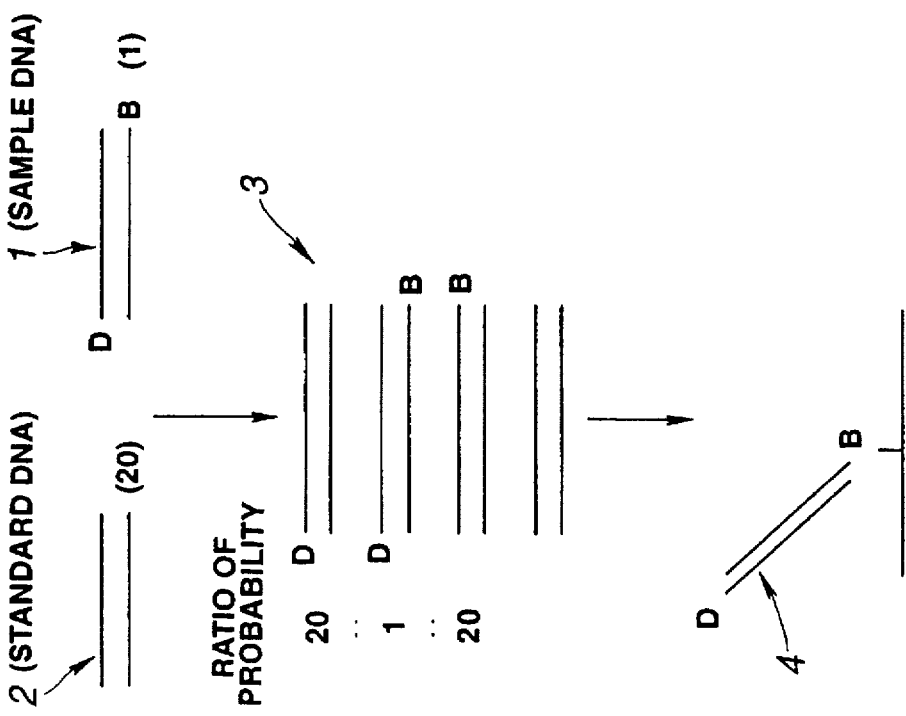

FIGS. 1A and 1B are schematic views of an example of detection wherein all sample DNA are identical to standard DNA. In the method of the present invention shown in FIG. 1(A), a gene to be assayed for mutation in a sample is amplified using a pair of primers comprising a primer having a detectable label (D) introduced therein and a primer having a solid matrix-binding label (B) introduced therein, resulting in a product designated labeled sample DNA 1. Separately, the same gene is amplified with a pair of unlabeled primers with the same base sequence, resulting in a product designated unlabeled standard DNA 2. Next, the labeled sample DNA 1 and the unlabeled standard DNA 2 are mixed at a ratio of 1:20, followed by denaturing and annealing, for effecting competitive hybridization. As a result, the nucleic acid having the detectable label (D) on one end and the solid matrix-binding label (B) on the other end is diluted to 1/21 (see reference numeral 3). Next, the reaction product is trapped on a solid phase matrix to measure the amount of the original labeled sample DNA 1 having undergone no recombination (see reference numeral 4). In this regard, the measurement is theoretically 1/21 (0.048) of the initial measurement.

On the other hand, in the method of Nicolas et al. shown in FIG. 1(B), an unlabeled sample DNA 1' and a labeled standard DNA 2' having introduced a detectable label (D) in one strand and a solid matrix-binding label (B) in the other strand are mixed at a ratio of 20:1, followed by denaturing and annealing, for effecting competitive hybridization (at reference numeral 3'). Next, the reaction product is trapped on a solid phase matrix to measure the amount of the original labeled standard DNA 2' having undergone no recombination (at reference numeral 4'). Then, as in the method of the present invention, the labeled standard DNA 2' having the labels (B) and (D) is also diluted to 1/21 as a result of competitive hybridization and the measurement is theoretically 1/21 (0.048) of the initial measurement.

Therefore, when the base sequence of the gene in the sample is completely identical with that of the standard DNA, the measurement after the competitive hybridization is theoretically 1/21 (0.048) of the initial measurement for both the inventive method and the conventional method (of Nicholas).

Figure 2A:
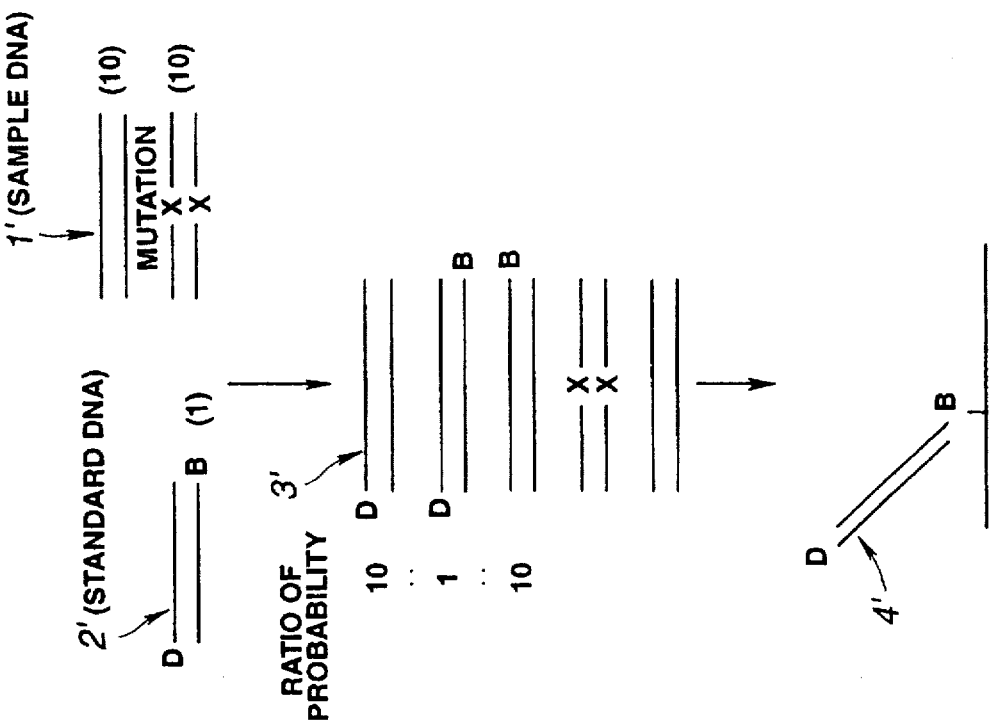
FIGS. 2A and 2B are schematic views illustrating nucleic acid differentiation methods as applied to nucleic acids one-half of which are mutant, FIG. 2A showing the method of the present invention and FIG. 2B showing a prior art method of Nicolas et al.
Figure 2B:
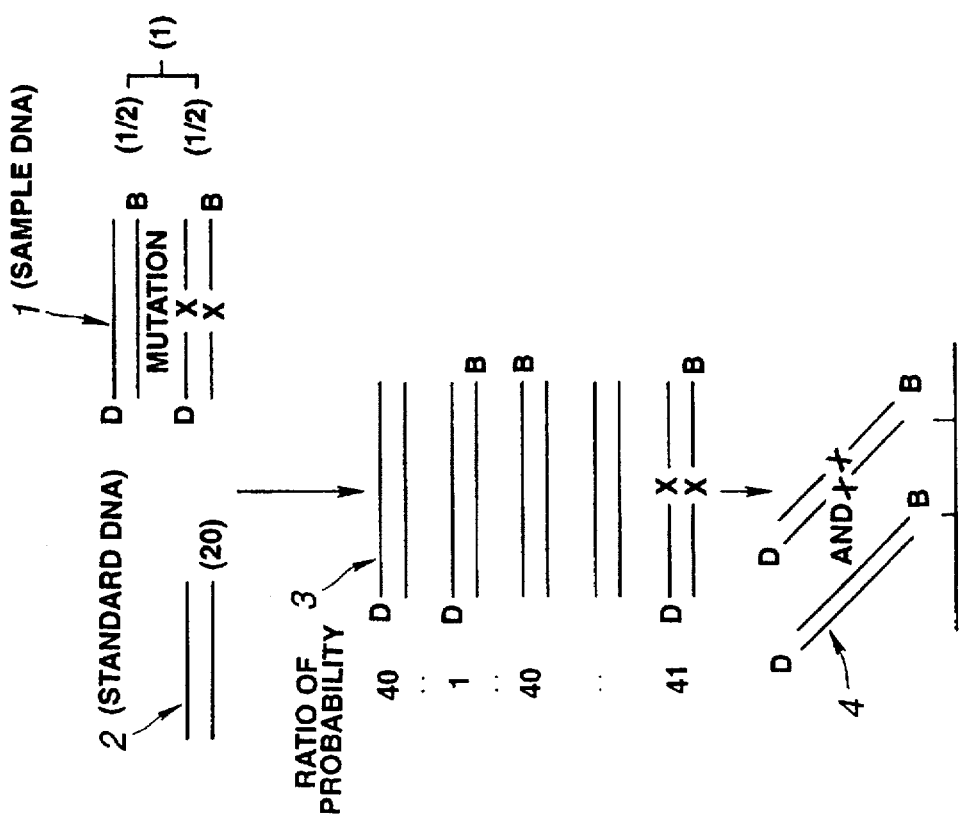

Next, an example wherein one of alleles in a sample is mutant is shown in the schematic views of FIGS. 2A and 2B.

Both the inventive method and the conventional method (Nicolas method) are carried out in accordance with a procedure as shown in FIGS. 1A and 1B by mixing sample DNA 1 or 1' with standard DNA 2 or 2' (at a ratio of 1:20 in the inventive method and 20:1 in the conventional method), followed by denaturing and annealing to effect competitive hybridization. Next, the reaction product 3 or 3' is trapped on a solid phase matrix to measure the amount of the original labeled DNA having undergone no recombination (reference numeral 4 or 4'). In this regard, according to the inventive method, the synthesized DNA having the labels (D) and (B) is diluted to 42/82 as a result of competitive hybridization (reference numeral 3) and the measurement is theoretically 42/82 (0.51) of the initial measurement. On the other hand, according to the conventional method (Nicolas method), the original labeled DNA having the labels (D) and (B) and having undergone no recombination is diluted to 1/11 (0.091) as a result of competitive hybridization and the measurement is theoretically 1/11 (0.091) of the initial measurement.

Figure 3B:
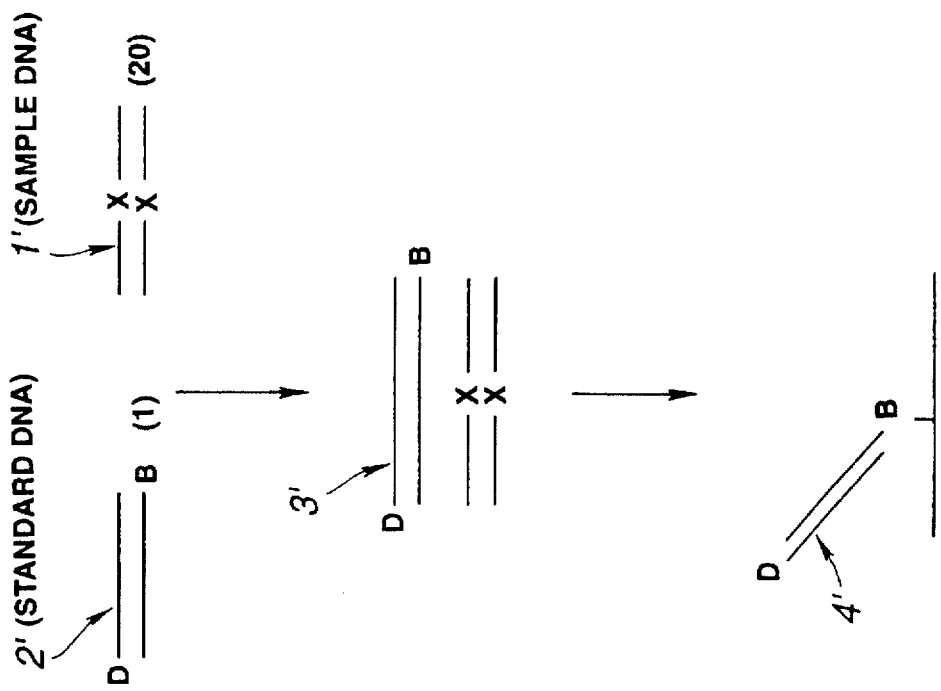
FIGS. 3A and 3B are schematic views illustrating nucleic acid differentiation methods as applied to all mutant nucleic acids, FIG. 3A showing the method of the present invention and FIG. 3B showing a prior art method of Nicolas.
Figure 3A:
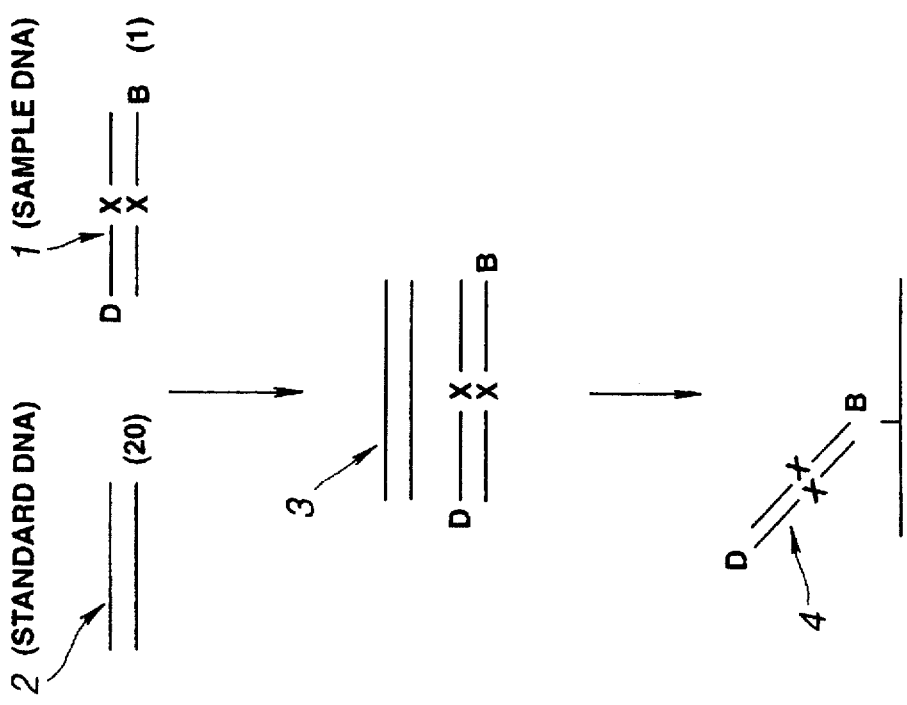

Further, where all genes in a sample are mutant, as shown in FIGS. 3(A) and 3(B), both the inventive method and the conventional method (Nicolas method) are carried out in accordance with a procedure as shown in FIGS. 1A, 1B, 2A and 2B by mixing sample DNA 1 or 1' with standard DNA 2 or 2' (at a ratio of 1:20 in the inventive method and 20:1 in the conventional method), followed by denaturing and annealing to effect competitive hybridization. The reaction product 3 or 3' is then trapped on a solid phase matrix to measure the amount of the original labeled DNA having undergone no recombination (reference numeral 4 or 4'). In both the inventive method and the conventional method (of Nicholas et al.), the labeled DNA having the labels (D) and (B) is not diluted at all as a result of competitive hybridization, and the measurement is theoretically the same as the initial measurement.

Table 1 summarizes a change of the measurement of the original labeled DNA having undergone no recombination with the proportion of a mutant gene.

TABLE 1

| | Theoretical measuremnt (ratio to the initial measurement of 1) | | |
|---|---|---|---|
| | All genes are normal | Half genes are mutant | All genes are mutant |
| Conventional method | 0.048 | 0.091 | 1 |
| Inventive method | 0.048 | 0.512 | 1 |

As is evident from Table 1, the measurement obtained in the inventive method differ by about 0.5 between the example wherein all genes in a sample to be assayed for mutation are normal, the example wherein half genes are mutant, and the example wherein all genes are mutant, with which clear differentiation among these example is possible. The measurements obtained in the conventional method (Nicolas method) differ only by 0.043 between the example wherein all genes are normal and the example wherein half genes are mutant, with which clear differentiation between these examples is impossible. Additionally, it is theoretically recognized that the inventive method provides a linear correlation between the proportion of mutant gene and the measurement.

Accordingly, the nucleic acid differentiating method of the present invention can detect the presence/absence of mutation independent of the ratio of normal to mutant genes. In addition, since there is a linear correlation between the ratio of normal to mutant genes in a sample and the measurement obtained by quantitating the molecule resulting from competitive hybridization and having both the solid matrix-binding label and the detectable label, the ratio of normal to mutant genes may be rather easily calculated from the measurement obtained. Furthermore, the inventive method can determine the matching of a particular gene in a plurality of DNA specimens by using the DNA specimens as the sample DNA and the standard DNA.

As described above, the nucleic acid differentiating method of the present invention first carries out gene amplification in a particular region of the target nucleic acid in a specimen by employing target nucleic acid-amplifying primers comprising a primer having a detectable label introduced therein and a primer having a solid matrix-binding site introduced therein.

The specimen to be assayed includes blood, tissue lesion and excretions such as feces and urine of human origin. When it is desired to carry out prenatal diagnosis, fetus cells in amniotic fluid or cells of cleaved oocyte in a test tube may be used as the specimen. The specimen may be used as such or if desired, prior to use, concentrated as a concentrate by centrifugation or the like, subjected to cell disruption by enzymatic treatment, heat treatment, surfactant treatment, ultra-sonication, or a combination thereof. In this regard, the cell disruption treatment is done for the purpose of exposing the DNA derived from the particular tissue of interest. The cell disruption may be carried out in accordance with any of the know methods described in the literature such as "PCR PROTOCOLS", Academic Press Inc., P14, P352, 1990. The specimen preferably contains the DNA of interest in a total amount of from about 1 to about 100 μg although less than 1 μg of DNA can still be amplified satisfactorily.

Next, the target nucleic acid-amplifying primers consist of a primer having a detectable label introduced therein and a primer having a solid matrix-binding site introduced therein. The detectable label or the solid matrix-binding site may be introduced in the primer at a position that would not adversely affect the elongation efficiency of the primers. Preferred positions of introduction are a hydroxyl group near the 5'-terminal and an active group in the base or phosphodiester moiety.

The detectable label employed herein may be either radioactive or non-radioactive, with use of a non-radioactive substance being preferred. The non-radioactive labels that can be directly introduced include fluorescent substances such as fluorescein derivatives (fluorescein isothiocyanate etc.) and rhodamine and its derivatives (tetramethylrhodamine isothiocyanate etc.); chemiluminescent substances (e.g., acridine etc.); and substances exhibiting delayed fluorescence (DTTA manufactured by Pharmacia).

Also the label may be indirectly detected by utilizing a substance that is capable of specifically binding with the label. The labels that can be used for such indirect labeling include biotin, ligands, particular nucleic acids or proteins, and haptens. In the case of biotin, avidin or streptavidin capable of specifically binding therewith may be used. In the case of haptens, antibodies capable of specifically binding therewith may be used. In the case of ligands, receptors may be used. In the case of particular nucleic acids or proteins, nucleic acids capable of specifically binding therewith, nucleic acid-binding proteins, or proteins having affinity to the particular protein may be used.

The haptens that can be used include compounds having a 2,4-dinitrophenyl group and digoxigenin. Biotin or fluorescent substances may also be used as a hapten. Such labels may be introduced alone or in combination of two or more, if desire, by a well-known technique (see JP-A 59-93099, 59-148798 and 59-204200). The detectable label may be identical with the solid phase-binding site.

When the target nucleic acid-amplifying primers are added to the specimen, gene amplification reaction based on elongation of the primers should take place if the target nucleic acid to be detected is present in the specimen.

In this regard, the elongation of the primers proceeds in terms of incorporation by the primers of the four types of nucleotide triphosphates (deoxyadenosine triphosphate, deoxyguanosine triphosphate, deoxycytidine triphosphate, and thymidine triphosphate; a mixture thereof is sometimes referred to as dNTP) as the substrates.

In carrying out the elongation reaction, an amplification reagent comprising the unit nucleic acids described above and a nucleic acid-elongating enzyme is generally employed for amplifying nucleic acid strands. The nucleic acid-elongating enzyme which can be used herein may be any DNA polymerase such as E. coli DNA polymerase I, Klenow fragments of E. coli DNA polymerase I and T4 DNA polymerase. However, use of thermally stable DNA polymerases such as Taq DNA polymerase, Tth DNA polymerase and Vent DNA polymerase is preferred since they can enhance the specificity of target sequence recognition by the primers to carry out rapid, specific gene amplification reaction (for more detail, see JP-A 1-314965 and 1-252300). In carrying out this reaction, oil may be added to the reaction system in order to prevent water from evaporating from the reaction solution. The oil used may be any oil which can be partitioned from water and has a lower specific gravity than water. Exemplary oils are silicone oil and mineral oil. Some gene amplification apparatus do not require such media, and the elongation of the primers may be promoted in such gene amplification apparatus.

As described above, the nucleic acid in the specimen may be efficiently amplified by repeating the elongation reaction using the nucleic acid-amplifying primers. The particular procedure for carrying out the gene amplification reaction including reaction conditions may be determined in accordance with the well-known methods described in the literature, for example, Jikken Igaku (Experimental Medicine), Yohdo-sha, 8, No. 9, 1990 and PCR Technology, Stockton Press, 1989.

Next, using the labeled DNA resulting from the above-mentioned gene amplification as the sample DNA and an unlabeled DNA specimen which is to be evaluated for its matching with the sample DNA as the standard DNA, at least an equimolar amount of the standard DNA is added to the sample DNA to effect competitive hybridization.

In this regard, the unlabeled standard DNA which is to be evaluated for its matching with the sample DNA is ideally one wherein both terminals are equal to the terminals of the sample DNA. However, both the terminals of the unlabeled standard DNA may not be completely equal. Example 5 to be described later used a standard DNA and a sample DNA which were different in length by three bases at both terminals, and still, the differentiation assay of sufficient precision could be carried out. As a practical measure, it seems preferable that the difference in strand length between the sample and standard DNA's is within about 10 bases at each terminal although the tolerable difference somewhat varies with the sequence of the target gene or the like.

The unlabeled standard DNA may be prepared through amplification reaction of a normal gene by using unlabeled primers having the same base sequence as the above-described primers used for gene amplification reaction. The thus amplified gene may be mass produced by incorporating it in a plasmid vector and propagating in *E. coli* or the like. Furthermore, a number of normal genes may be tandemly ligated before incorporating in the plasmid to facilitate the mass production. Alternatively, the standard DNA can be prepared by direct enzymatic excision from a natural gene without resorting to gene amplification, or in some cases, by chemical synthesis.

For incorporating such tandemly ligated unlabeled standard DNAs in the plasmid, a sequence recognizable by the restriction enzyme used for the tandem ligation of the standard genes in the same direction and a sequence recognizable by the restriction enzyme used for the excision of the unlabeled DNA are introduced into a pair of primers used for amplification at their 5'-terminals. The sequence recognizable by the restriction enzyme used for the tandem ligation of the standard genes in the same direction may preferably be one having an asymmetric sequence left at the cleaved end, and more preferably, SfiI or the like that recognizes 8 bases. The recognizable sequence should be the one that is absent in the standard DNA. The sequence recognizable by the restriction enzyme used for the excision of the unlabeled DNA is preferably one having a blunt end left therein although ones having another end left therein may also be used. The recognizable sequence selected should be the one that is absent in the standard DNA. The vector that transports the DNA may be any vector such as a plasmid or a phage. The preferred is a vector of a large copy number which can be propagated in *E. coli*, for example, pUC118 which is suitable for mass production.

In one illustrative procedure for excising the unlabeled standard DNA from the plasmid in which the unlabeled standard DNA has been introduced, the sequence used as the standard DNA is amplified by using a pair of primers having introduced at their 5'-terminals a sequence recognizable by the restricting enzyme for the tandem ligation of the standard genes in the same direction and a sequence recognizable by the restriction enzyme used for the excision of the unlabeled DNA, followed by cleavage with the restriction enzyme for tandem ligation. The cleaved sequence are ligated to prepare a sequence wherein a plurality of standard DNAs are tandemly ligated. This is incorporated into the vector to prepare a plasmid having incorporated therein the standard DNAs tandemly ligated in the same direction. Treatment of the plasmid with the restriction enzyme use for excision of the standard DNA would produce the standard DNA.

In this regard, a larger number of repetition after ligation is preferred. A number of 10 to several tens seems appropriate for such requirements as the stability of the plasmid although the number depends on the sequence of the standard DNA.

Next, according to the invention, competitive hybridization is carried out between the labeled sample DNA and the unlabeled standard DNA which is previously prepared by the above-mentioned procedure. Both the DNAs should be denatured in the competitive hybridization while the denaturing technique is preferably a thermal or alkaline technique. Both the DNAs may be mixed together either immediately before denaturing or after denaturing. In the inventive method, at least an equimolar amount, typically a 5 to 20-fold molar excess amount of the unlabeled standard DNA should be added to the labeled sample DNA although the optimum ratio varies with the length, base sequence, degree of mutation of the DNA.

Furthermore, in the competitive hybridization, the solution should be adjusted to an optimum salt concentration, which largely depends on the strand length. In general, SSC (20×SSC: 3M sodium chloride, 0.3M sodium citrate) and SSPE (20×SSPE: 3.6M sodium chloride, 0.2M sodium phosphate, 2 mM EDTA) are used in hybridization and in the practice of the invention, these solutions may be used after diluting to a suitable concentration.

The competitive hybridization may be accomplished by mixing the labeled sample DNA and the unlabeled standard DNA which are denatured by the above-mentioned procedure, and slowly cooling the mixture from an elevated temperature. With respect to the temperature conditions, optimum conditions may be suitably determined in consideration of the length of DNA strands being hybridized, the base sequence, the difference between the normal and mutant base sequences. One typical condition is to lower the temperature at a rate of 1° C. per 3 to 10 minutes in the temperature range from 98° C. to 58° C.

Next, the product of competitive hybridization is measured by the principle of ED-PCR method (see, for example, JP-A 1-314965 and 1-252300 and Ubukata et al. J. Clin. Micobiol. 30, 1728, 1992). The ED-PCR method can express the presence of a duplex strand nucleic acid as a signal only when the strands of the duplex strand nucleic acid have different labels (or identical labels as the case may be). Therefore, in the above-described product of competitive hybridization, the signal will become lower as the frequency of strand substitution between the labeled sample DNA and the unlabeled standard DNA increases. In other words, the signal will become lower as the sample contains a larger proportion of the same base sequence as the unlabeled standard DNA in the region of interest. If desired, the label may be introduced into only one strand of the sample DNA and into the complementary strand of the standard DNA whereby a signal is developed when the sample DNA has a base sequence that matches with that of the standard DNA, namely when strand substitution occurs between the sample and standard DNAs.

As described above, the product of competitive hybridization is measured, and then, sequence matching of the sample DNA with the standard DNA is determined from the measurements (to find out the presence/absence of the mutant gene, the ratio of mutant to normal genes, any difference in base sequence between the sample DNA and the standard DNA, and a degree of such difference). Any conventional technique may be employed for the measurement depending on the label used. For example, when the label used is a radioisotope, simply radioactivity may be measured, and when the label is a fluorescent substance, simply fluorescence intensity may be measured with a fluorometer (see JP-A 1-252300).

On the other hand, when a label other than the directly detectable label is introduced in the primer, a reagent that enables an indirect measurement of the introduced label is utilized. Exemplary reagents used for such measurement are a complex of avidin or streptavidin with an enzyme when the label is biotin; and an antibody-enzyme complex wherein an antibody capable of specifically binding to the hapten is bound to an enzyme and a substrate for the enzyme when the label is a hapten. When such a reagent is used, the reagent reacts with the label to produce a component that can be detected by color or fluorescent means. With respect to the enzyme and substrate that may be used in such reagents, 2-nitrophenol, β-D-galactoside, 4-methylumbeliferyl-β-D-galactoside, etc. may be used as the substrate when the enzyme is β-D-galactosidase; 3-(4-hydroxyphenyl) propionic acid, 3,3',5,5'-tetramethylbenzidine, 1,2-phenylenediamine, etc. may be used as the substrate when the enzyme is peroxidase; 4-methylumbeliferyl phosphate, NADP, 4-nitrophenyl phosphate, etc. may be used as the substrate when the enzyme is alkaline phosphatase; glucose, NAD, etc. may be used as the substrate when the enzyme is glucose-6-phosphate dehydrogenase; and ethanol, NAD, etc. may be used as the substrate when the enzyme is alcohol dehydrogenase.

The measurement of the hybridization product is carried out by trapping it on a solid phase matrix. The solid phase matrix used herein is the one capable of specifically binding with the solid matrix-binding site that has been introduced in the primer. An exemplary solid phase matrix is a microtiter plate which is pretreated so that microtiter wells may specifically bind with the matrix-binding site of the primer.

The results of measurement are described below. When no mutation is present in the gene region of interest in the sample, the measurement will have a significantly low value because of dilution with the excess of the unlabeled standard DNA as previously described in conjunction with the schematic view of FIGS. 1 to 3. When all genes are mutant, the measurement will have a high value since the labeled DNA is not diluted with the unlabeled standard DNA. When half genes are mutant (when either one of alleles is mutant), the measurement will have a value intermediate the value associated with nil mutation and the value associated with all mutant genes. Such a specimen can be easily differentiated.

Furthermore, if a calibration curve showing the measurement in relation to the ratio of mutant to normal genes is depicted by previously measuring various sample DNAs having different ratios of mutant to normal genes, then the ratio of gene to normal genes in a specimen will be readily determined from an actual measurement.

If the type of HLA is determined by conventional methods (PCR-SSO method (K. Randall et al., Nature, 324, 163, 1986); PCR-RFLP method (N. Maeda et al., Tissue Antigens, 34, 290, 1989); PCR-SSP method (O. Lerup et al., Tissue Antigens, 39, 225, 1992)), the results that alleles in the sample are homoallelic leave a risk of inaccurate determination since there is a possibility that the sample is hetero-allelic to an unknown type. However, the method of the present invention can definitely conclude whether the sample is homoallelic. In addition, when analysis is made according to the inventive method by using the DNA of one specimen amplified with a labeled primer as the labeled DNA, and using the DNA of another specimen amplified with an unlabeled primer having the same sequence as the unlabeled standard DNA, the DNAs of the two specimens examined can be confirmed whether alleles in the DNAs are in complete conformity with one another. This would be an effective means for final confirmation in a transplantation surgery.

Next, the assay kit for nucleic acid differentiation according to the present invention is to determine the sequence matching of nucleic acids by the above-described nucleic acid differentiating method of the present invention. As described above, this assay kit comprises gene amplifying primers for amplifying the gene in a particular region of the target nucleic acid, and an unlabeled standard DNA to be evaluated for is matching with the gene amplified with said primers.

The gene amplifying primers for amplifying the gene in a particular region of the target nucleic acid includes a primer having a detectable label introduced therein and a primer having a solid matrix-binding site introduced therein. The detectable label and the solid matrix-binding site are the same as previously described in conjunction with the nucleic acid differentiating method of the present invention. The unlabeled standard DNA is also the same as previously described in conjunction with the method of the present invention.

The assay kit for nucleic acid differentiation according to the present invention is used in accordance with the above-described nucleic acid differentiating method of the present invention by mixing the gene amplifying primers with a specimen that has optionally been subject to a pretreatment such as cell disruption and adding amplifying reagents to the mixture, amplifying a particular region of the target nucleic acid in the specimen, adding the unlabeled standard DNA thereto, allowing competitive hybridization to take place, trapping the hybrid on a matrix to measure a degree of recombination between the sample DNA and the standard DNA. The amplifying reagents and matrix used herein may be those known in the art, more particularly those examples previously described for the nucleic acid differentiating method of the present invention. The nucleic acid discriminating assay kit of the present invention can be completed by combining with such amplifying reagents and matrix.

Furthermore, in carrying out assay for nucleic acid differentiation with the assay kit according to the present invention, there may be used a cell disruption reagent for specimen pretreatment, a washing solution for washing the amplified product, an oil for preventing water evaporation from the reaction solution, a reagent for indirectly measuring the label and other components as previously described for the nucleic acid differentiating method of the present invention. The nucleic acid discriminating assay kit of the present invention can be completed by further combining with such components.

Examples and Comparative Example are given below for further illustrating the present invention although the present invention is by no means limited by the Examples.

EXAMPLE 1

A point mutation, Glu (GAG)→Val (GTG) in 6th codon of human β globin gene was detected as follows.

The target gene used was a DNA fragment of about 200 bp which could be amplified by amplifying primers, PBG-1 (SEQ. ID. NO.1) and PG-2 (SEQ. ID. NO.2) as described below.

PBG-1

| 5'GGGTTGGCCAATCTACTCCCAG | (SEQ ID NO:1) |

PG-2

| 5'CAACTTCATCCACGTTCACC | (SEQ ID NO:2) |

Amplification of the DNA by the PCR technique was carried out by using PBG-1-$NH_2$ (100 ng) and PG-2-$NH_2$ (100 ng) with pBGN (1 ng) or PBGM (1 ng) as described below as a template in the presence of 200 μM of four types of dNTP in 100 μl of a reaction solution containing 67 mM trishydrochloric acid buffer (pH 8.8), 16.6 mM $(NH_2)_2SO_4$, 6.7 mM $MgCl_2$, 10 mM 2-mercaptoethanol, and 2 units of Tth DNA polymerase. The reaction was performed by heating the reaction system at 94° C. for 5 minutes and repeating 30 cycles of 94° C. for 30 seconds, 50° C. for 30 seconds, and 72° C. for 60 seconds. The resulting reaction solution was used as an unlabeled standard DNA solution.

Separately, PG-2-DNP (100 ng) and PBG-1-BiO (100 ng) with pBGN (1 ng) or pBGM (1 ng) were mixed and amplification by PCR technique was carried out in the presence of 200 µM of four types of dNTP under the same conditions as described above. There was obtained a labeled sample DNA solution.

PBG-1-Bio

Biotin-5'GGGTTGGCCAATCTACTCCCAG    (SEQ ID NO:1)

PG-2-DNP

DNP-5'CAACTTCATCCACGTTCACC    (SEQ ID NO:2)

PBG-1-NH$_2$

NH$_2$-5'GGGTTGGCCAATCTACTCCCAG    (SEQ ID NO:1)

PG-2-NH$_2$

NH$_2$-5'CAACTTCATCCACGTTCACC    (SEQ ID NO:2)

pBGN

A plasmid having normal human β-globin gene pBGM

A plasmid having one base mutation,

Glu (GAG)→Val (GTG) at 6th amino acid

The amplified products in the standard DNA solution and sample DNA solution were respectively confirmed for their size by agarose gel electrophoresis to find that they were produced in substantially the same amount.

Competitive hybridization

The standard DNA solution and the sample DNA solution were mixed, and water was added to 30 µl. 6 µl of 20×SSC (0.3M sodium citrate, pH 7.0, 0.3M sodium chloride) was added to the mixture, and mineral oil was overlaid. The mixture was heated to 98° C. for 10 minutes, and gradually cooled to 58° C. at a rate of 1° C. per 6 to 10 minutes using a gene amplifier (Thermal-Cycler PJ2000, Perkin-Elmer). A 20-µl aliquot was taken out of the reaction solution for detection. Note that the unlabeled standard DNA solution used was derived from the pBGN. The labeled sample solution used was derived from the pBGN or pBGM, or a mixture of them in equal amounts. Analysis was made while varying the volume ratio of the unlabeled standard DNA solution to the labeled sample DNA solution.

Detection

The molecules resulting from competitive hybridization and simultaneously having both the biotin label and the DNP label on the 5'-terminal of each strand are detected.

To a microtiter plate having immobilized thereon streptavidin is added 100 µl of 50 mM tris-hydrochloric acid (pH 7.5), 0.15M NaCl, and 0.05% Tween 20 containing an anti-DNP mouse IgG-alkaline phosphatase complex. 20 µl of the hybridization solution was added thereto. After admixing, the plate was incubated at 25° C. for 30 minutes and washed three times with 300 µl of the same solution except antibody-enzyme complex. To this microtiter plate was added 100 µl of 1M diethanolamine (pH 9.8) and 0.5 mM MgCl$_2$ containing 4 mg/ml of p-nitrophenyl phosphate, and color development was effected at 25° C. for 1 hour. The yellow color developed was measured in terms of absorbance at 405 nm using a plate reader. It should be noted that hybridization was simultaneously carried out in two tubes, and the measurements were averaged.

Competitive hybridization was carried out while varying the mixing ratio of the standard DNA solution to the sample DNA solution. The resulting "duplex strand DNA having the DNP label on one strand and the biotin label on the other strand" was detected. The results are shown in Table 2.

TABLE 2

| Standard DNA (unlabeled) | Sample DNA (labeled) | Standard:sample ratio | Absorbance (A405) |
|---|---|---|---|
| Noraml (pBGN) | Normal (pBGN) | 20:1 | 0.120 |
| Noraml (pBGN) | Mix of normal (pBGN) and mutant (pBGM) | 20:1 | 0.418 |
| Noraml (pBGN) | Mutant (pBGM) | 20:1 | 0.988 |
| Noraml (pBGN) | Normal (pBGN) | 10:1 | 0.202 |
| Noraml (pBGN) | Mix of normal (pBGN) and mutant (pBGM) | 10:1 | 0.511 |
| Noraml (pBGN) | Mutant (pBGM) | 10:1 | 1.068 |
| Noraml (pBGN) | Normal (pBGN) | 5:1 | 0.369 |
| Noraml (pBGN) | Mix of normal (pBGN) and mutant (pBGM) | 5:1 | 0.631 |
| Noraml (pBGN) | Mutant (pBGM) | 5:1 | 1.150 |

Comparative Example

Mutation in nucleic acid was detected according to the conventional method. The standard DNA solution prepared by using the labeled primers was mixed with an excessive amount of the sample DNA solution prepared by using the unlabeled primers and competitive hybridization effected (The solutions were mixed so that the molar ratio of labeled DNA to unlabeled DNA was 1:20). The remaining reaction conditions were the same as in Example 1. The results are shown in Table 3.

TABLE 3

| Standard DNA | Sample | Absorbance (A405) |
|---|---|---|
| Normal (pBGN) | Normal | 0.16 |
| Normal (pBGN) | Normal + Mutant | 0.20 |
| Normal (pBGN) | Mutant | 1.02 |

As shown in Table 3, the conventional method affording only a difference of 0.04 in absorbance between the normal DNA and the normal DNA+mutant DNA was quite difficult to differentiate these samples from each other compared with Example 1 according to the inventive method.

EXAMPLE 2

A mutation, GGC (Gly)→GTC (Val) in 12th codon of human c-H-ras gene was detected as follows. In this example, a DNA fragment of about 110 bp containing a mutant position obtained by amplifying pSK-2 or pKY-1 as described below with primers, PHR-1 (SEQ. ID. NO.3) and PHR-2 (SEQ. ID. NO.4) was used for experiment.

Amplification was carried out as in Example 1 using the primers, PHR-1-DNP (100 ng) and PHR-2-Bio (100 ng) as described below with pSK-2 or pKY-1 (1 ng) as described below as a template, obtaining a labeled sample DNA solution. Separately, pSK-2 was amplified with the primers, PHR-1-NH$_2$ and PHR-2-NH$_2$ as described below, obtaining an unlabeled standard DNA solution. The amplified products were confirmed for their amount and length by agarose gel electrophoresis.

PHR-1

5'ATGACGGAATATAAGCTGGTG    (SEQ ID NO:3)

PHR-2

5'CTCTATAGTGGGGTCGTATTC    (SEQ ID NO:4)

PHR-1-DNP

DNP-5'ATGACGGAATATAAGCTGGTG    (SEQ ID NO:3)

PHR-2-Bio

Bio-5'CTCTATAGTGGGGTCGTATTC    (SEQ ID NO:4)

PHR-1-NH$_2$

NH$_2$-5'ATGACGGAATATAAGCTGGTG    (SEQ ID NO:3)

PHR-2-NH$_2$

NH$_2$-5'CTCTATAGTGGGGTCGTATTC    (SEQ ID NO:4)

pSK-2

A plasmid containing normal ras gene (T. Sekiya, Gann, 74, 794, 1983) available from JCRB (Japan Cancer Research Resources Bank).

pKY-1

A plasmid having a mutation at 12th codon (M. H. Kraus and Y. Yuasa, Nature, 303, 775, 1983) available from JCRB (Japan Cancer Research Resources Bank).

Competitive hybridization and detection

The standard DNA solution and the sample DNA solution were mixed, and water was added to 30 μl. 6 μl of 20×SSC was added to this mixture and the detection was carried out as in Example 1. It should be noted that competitive hybridization was simultaneously carried out in two tubes, and the measurements were averaged. The results are shown in Table 4.

TABLE 4

| Standard DNA solution | Sample DNA solution | Standard:sample ratio | Absorbance (A405) |
|---|---|---|---|
| Normal (pSK-2) | Normal | 20:3 | 0.122 |
| Normal (pSK-2) | Normal +Mutant | 20:3 | 0.338 |
| Normal (pSK-2) | Mutant | 20:3 | 0.575 |

The results of Tables 2 and 4 reveal that the nucleic acid differentiating method of the present invention was effective for establishing a definite discrimination among the sample wherein both alleles are normal, the sample wherein one allele is mutant, and the sample wherein both alleles are mutant since the respective samples exhibited significant changes of absorbance. On the contrary, the conventional method (of Nicholas et al.) failed to differentiate the sample wherein both alleles are normal and the sample wherein one allele is normal and the other allele is mutant since there was no significant difference between them.

EXAMPLE 3

By adding a minute amount of mutant DNA (oncogene) to normal DNA as a model simulating a state wherein cells having a particular mutant gene are mixed with normal cells, an experiment was carried out as follows, to see whether such a state could be detected by the inventive method.

Human c-H-ras gene (derived from pSK-2) was used as the normal DNA, and human c-H-ras gene having a mutation, GGC (Gly)→GTC (Val) in 12th codon (derived from pKY-1) was used as the mutant DNA. Samples were prepared so that they contained the mutant DNA at a percentage of 0%, 5%, 10%, 25%, 50% and 100% based on the normal DNA. These samples were amplified using a pair of primers, PHR-1-DNP and PHR-2-Bio, obtaining a labeled sample DNA solution.

Separately, normal DNA was amplified using a pair of primers, PHR-1-NH$_2$ and PHR-2-NH$_2$, obtaining an unlabeled standard DNA.

The labeled sample DNA solution and the unlabeled standard DNA solution were mixed so as to give a molar ratio of DNAs of 1:20 in the combined solution, followed by thermal denaturing and annealing. Detection was made as in Example 1. The results are show in Table 5. Also the absorbance is diagrammatically plotted relative to the ratio of mutant to normal genes based on an absorbance of 1 for the sample wherein the proportion of the mutant DNA in relation to the normal DNA is 100%. This is shown in FIG. 4.

TABLE 5

| Proportion of mutant DNA relative to normal gene | Absorbance (A405) |
|---|---|
| 0% | 0.045 |
| 5% | 0.079 |
| 10% | 0.101 |
| 25% | 0.146 |
| 50% | 0.304 |
| 100% | 0.563 |

Figure 4:
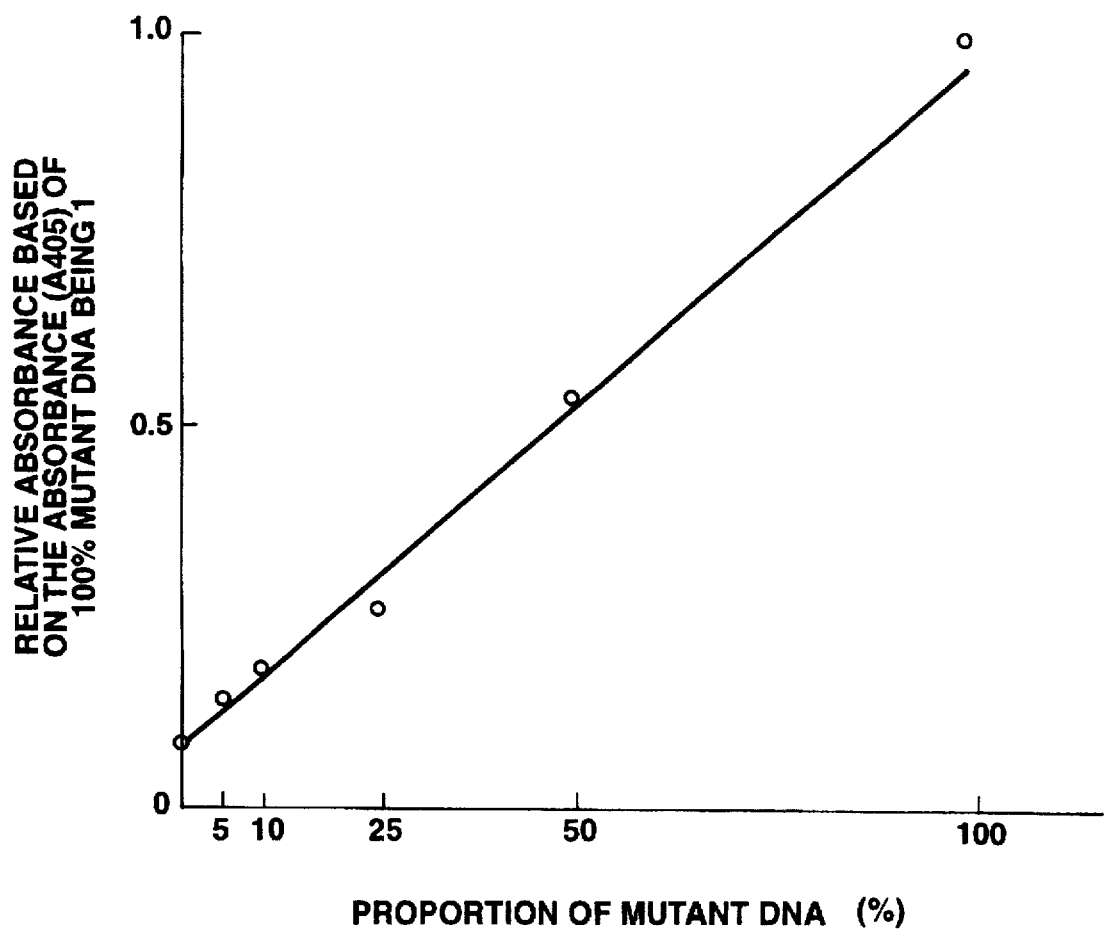
FIG. 4 is a graph showing the absorbance relative to the proportion of mutant in a sample DNA as processed by the nucleic acid differentiating method of the present invention.

The results shown in Table 5 and FIG. 4 reveal that a significant difference in absorbance is observed even when the proportion of mutant DNA to normal DNA is low, that there is a clear correlation between the mutant DNA proportion and the absorbance, and that detection is easy even when the amount of mutant DNA is as low as about 10%. Accordingly, for DNA diagnosis wherein a minute amount of cancer cells must be detected from various tissues present in blood, urine or feces, assay by the inventive method enables not only to detect the presence of the cells with the mutant DNA, but also to approximately calculate the ratio of cells with mutant DNA.

EXAMPLE 4

Genetic diagnosis of cystic fibrosis

Human CFTR (cystic fibrosis transmembrane conductance regulator) gene is believed to be a gene responsible for cystic fibrosis. This disease is manifested only when both alleles of this gene are abnormal, and those having abnormality only on one allele would not suffer from this disease, but would be carriers who transmit the causal genes to their descendant. Therefore, the genetic diagnosis of CFTR requires differentiation among the cases wherein both alleles are mutant, wherein only one allele is mutant, and wherein both alleles are normal.

About 70% of the mutations found in this gene result from deletion of 508th phenyl-alanine. However, there have been found many other types of mutations while their position and type are diversified and non-specific.

17

The inventive method aims to determine whether both alleles are normal, only one allele is mutant or both alleles are mutant with respect to the specific region which is regarded prone to mutation based on the previous reports.

In this Example, experiments were carried out for four typical mutations shown in Table 6, below. It would be possible to readily construct a detection system for other mutations. Although this Example shows only models having one mutation per exon, a mutation other than that detected in this Example can also be detected when the mutation is present in the amplified product.

TABLE 6

| Exon | Type of the mutation |
|------|----------------------|
| Exon 4 | 621 + 1G > T |
| Exon 10 | Δ F508 |
| Exon 11 | G551D |
| Exon 21 | N1303K |

(1) Examination of exon 4
Preparation of a sample

A part of exon 4 was amplified by using human chromosome DNA as a template, and incorporated into primers CF04P101 (SEQ. ID. NO.5) and CF04M101 (SEQ. ID. NO.6) as shown below.
CF04P101

5'ATTGTGAGGACACTGCTCCTACACCCAGCC

CF04M101

5'TACGATACAGAATATATGTGCCATGGGGCC

PCR amplification was carried out by using CF04P101-OH (100 ng) and CF04M101-OH (100 ng) with 1 µg of normal human chromosome as the template in the presence of 200 µM of four types of dNTP in 100 µl of a reaction solution containing 67 mM tris-hydrochloric acid buffer (pH 8.8), 16.6 mM $(NH_2)_2SO_4$, 6.7 mM $MgCl_2$, 10 mM 2-mercaptoethanol, and 2 units of Tth DNA polymerase. The reaction was performed by heating the reaction system to 94° C. for 5 minutes and repeating 35 cycles of 94° C. for 30 seconds, 60° C. for 30 seconds, and 72° C. for 60 seconds.

The reaction solution was separated by agarose electrophoresis to obtain a fragment of about 230 bp. This fragment was introduced into SmaI site of pUC119. With the base sequence confirmed, this was designated pEX4N.

A point mutation was introduced in the gene by the overlap extension mutagenesis technique (Steffan N. Ho et al., Gene, 77, 51–59, 1989) using the pEX4N as the template and using four primers, CF04P101 and CF04M101 as described above and CF04621P (SEQ. ID. NO.7) and CF04621M (SEQ. ID. NO.8) as described below, obtaining a gene of 621+1G>T. With the base sequence confirmed, this was designated pEX4M.
CF04621P

GATTTATAAGAAGTTAATACTTCCTTG
CACAG                          (SEQ ID NO:7)

CF04621M

AAGTATTAACTTCTTATAAATCAAACT    (SEQ ID NO:8)

Detection of mutant gene

An unlabeled standard DNA was prepared as described below.

18

PCR amplification was carried out by using CF04P101-$NH_2$ (100 ng) and CF04M101-$NH_2$ (100 ng) together with the above-mentioned pEX4N (1 ng) and also using a reaction solution of the same composition as used for the preparation of the sample.

Separately, a labeled sample DNA was prepared by carrying out PCR amplification using CF04P101-Bio (100 ng) and CF04M101-DNP (100 ng) together with a plasmid as described below as the template.

| Normal: | 1 ng of pEX4N |
|---------|---------------|
| Mutation in one allele: | 0.5 ng of pEX4N |
| | 0.5 ng of pEX4M |
| Mutation in both alleles: | 1 ng of pEX4M |

The amplified products in the standard DNA solution and the sample DNA solution were evaluated for size by agarose gel electrophoresis to find that the they were produced in a substantially equal amount.

Competitive hybridization

The sample DNA solution was mixed with a 20-fold amount of the standard DNA solution under the conditions of Example 1. The reaction solution was heated to 98° C. for 10 minutes, and the temperature was gradually decreased to 68° C. at a rate of 1° C./10 min. A 20-µl aliquot was taken out of the reaction solution, and the molecules resulting from competitive hybridization and having both the biotin and DNP labels on 5'-terminal of their strands were detected by the same procedure as in Example 1. The results are shown in Table 7.

TABLE 7

| Standard DNA solution (unlabeled) | Sample DNA solution (labeled) | Absorbance (A405) |
|-----------------------------------|-------------------------------|-------------------|
| Normal (pEX4N origin) | Normal (pEX4N) | 0.11 |
| Normal (pEX4N origin) | Mix of normal (pEX4N) and mutant (pEX4M) | 0.70 |
| Normal (pEX4N origin) | Mutant (pEX4M) | 1.87 |

As shown in Table 7, the cases wherein both alleles are normal, wherein only one allele is mutant, and wherein both alleles are mutant could be clearly distinguished.

(2) Examination of exon 10

With respect to exon 10, detection was carried out as follows using the most frequently found mutation ΔF508 as a model.

Preparation of the sample

Using CF10P101-OH (SEQ. ID. NO.9) (100 ng) and CF10M101-OH (SEQ. ID. NO.10) (100 ng) as described below together with human chromosome DNA (1 µg), PCR amplification was carried out by the above-described procedure. The amplified product was similarly introduced into a plasmid to produce pEX10N having the normal gene.
CF10P101

5'GATTATGGGAGAACTGGAGCCTTCAG
AGGG                           (SEQ ID NO:9)

CF10M101

5'CTTCTAGTTGGCATGCTTTGATGACGC
TTC                            (SEQ ID NO:10)

Separately, using four primers, CF10P101-OH and CF10M101-OH as described above and CFΔF508U (SEQ.

ID. NO.11) and CFΔF508L (SEQ. ID. NO.12) as described below together with pEX10N as the template, a plasmid pEX10M having mutation ΔF508 was produced by the overlap extension mutagenesis method.

CFΔF508U

5'AAATATCATCGGTGTTTCCTATGA (SEQ ID NO:11)

CFΔF508L

5'CACCGATGATATTTTCTTTAATG (SEQ ID NO:12)

Detection of gene mutation

A labeled sample DNA was prepared through PCR amplification using CF10P101-Bio (100 ng) and CF10M101-DNP (100 ng) as the primers together with a plasmid as described below as the template.

| Normal: | 1 ng of pEX10N |
| Mutation in one allele: | 0.5 ng of pEX10N |
|  | 0.5 ng of pEX10M |
| Mutation in both alleles: | 1 ng of pEX10M |

An unlabeled standard DNA was prepared through PCR amplification using CF10P101-NH₂ (100 ng) and CF10M101-NH₂ (100 ng) together with pEX10N (1 ng).

The sample DNA was analyzed by the same procedure as described for exon 4, with the results shown in Table 8. As shown in Table 8, the three gene types could be clearly distinguished.

TABLE 8

| Standard DNA solution (unlabeled) | Sample DNA solution (labeled) | Absorbance (A405) |
|---|---|---|
| Normal (pEX10N origin) | Normal (pEX10N) | 0.14 |
| Normal (pEX10N origin) | Mix of normal (pEX10N) and mutant (pEX10M) | 0.89 |
| Normal (pEX10N origin) | Mutant (pEX10M) | 1.74 |

(3) Examination of exon 11

With respect to exon 11, G551D was used as a model.

Preparation of a sample

Using CF11P101-OH (SEQ. ID. NO.13) (100 ng) and CF11M101-OH (SEQ. ID. NO.14) (100 ng) together with human chromosome DNA (1 μg), PCR amplification was carried out by the same procedure as described for exon 4. The amplified product was similarly introduced into a plasmid to produce a plasmid pEX11N having the normal gene.

CF11P101

5'GAAGGAAGATGTGCCTTTCAAATTCA GATTG (SEQ ID NO:13)

CF11M101

5'ATGACATTTACAGCAAATGCTTGCTA GACC (SEQ ID NO:14)

Separately, using four primers, CF11P101-OH and CF11M101-OH as described above and CF11-551P-OH (SEQ. ID. NO.15) and CF11-551M-OH (SEQ. ID. NO.16) as described below together with pEX11N as the template, a plasmid pEX11M having mutation G551D was produced by the overlap extension mutagenesis method.

CF11-551P

5'CACTGAGTGGAGATCAACGAGCAAGA ATTTCT (SEQ ID NO:15)

CF11-551M

5'GCTCGTTGATCTCCACTCAGTGTGATTC (SEQ ID NO:16)

Detection of gene mutation

An unlabeled standard DNA was prepared through PCR amplification using CF11P101-NH₂ (100 ng) and CF11M101-NH₂ (100 ng) together with pEX11N (1 ng).

A labeled sample DNA was prepared through PCR amplification using CF11P101-Bio (100 ng) and CF11M101-DNP (100 ng) together with a plasmid as described below as the template.

| Normal: | 1 ng of pEX11N |
| Mutation in one allele: | 0.5 ng of pEX11N |
|  | 0.5 ng of pEX11M |
| Mutation in both alleles: | 1 ng of pEX11M |

Using the resulting unlabeled standard DNA and labeled sample DNA, gene mutation was detected as described for exon 4. The results are shown in Table 9. As shown in Table 9, the three gene types could be clearly distinguished.

TABLE 9

| Standard DNA solution (unlabeled) | Sample DNA solution (labeled) | Absorbance (A405) |
|---|---|---|
| Normal (pEX11N origin) | Normal (pEX11N) | 0.08 |
| Normal (pEX11N origin) | Mix of normal (pEX11N) and mutant (pEX11M) | 0.48 |
| Normal (pEX11N origin) | Mutant (pEX11M) | 1.90 |

(4) Examination of exon 21

With respect to exon 21, N1303K mutation was used as a model.

Using CF21P101-OH (SEQ. ID. NO.17) (100 ng) and CF21M101-OH (100 ng) together with human chromosome DNA (1 μg), a plasmid pEX21N having normal gene was produced in accordance with the above-described procedure.

CF21P101

5'AGAGAACTTGATGGTAAGTACATGG GTGTT (SEQ ID NO:17)

CF21M101

5'TTAGCAGCCTTACCTCATCTGCAACT TTCC (SEQ ID NO:18)

Separately, using four primers, CF21P101-OH and CF21M101-OH as described above and CF21-1303P-OH (SEQ. ID. NO.19) and CF21-1303M-OH (SEQ. ID. NO.20) as described below together with pEX21N as the template, a plasmid pEX21M having N1303K mutation was produced by the overlap extension mutagenesis method.

CF21-1303P

5'CATTTAGAAAAAAGTTGGATCCCTAT GAACA (SEQ ID NO:19)

CF21-1303M

5'GGGATCCAACTTTTTTCTAAATGTTCCAG (SEQ ID NO:20)

Detection of gene mutation

An unlabeled standard DNA was prepared through PCR amplification using CF21P101-NH$_2$ (100 ng) and CF21M101-NH$_2$ (100 ng) with pEX21N (1 ng).

A labeled sample DNA was prepared through PCR amplification using CF21P101-Bio (100 ng) and CF21M101-DNP (100 ng) together with a plasmid as described below as the template.

| Normal: | 1 ng of pEX21N |
|---|---|
| Mutation in one allele: | 0.5 ng of pEX21N |
| | 0.5 ng of pEX21M |
| Mutation in both alleles: | 1 ng of pEX21M |

Using the resulting unlabeled standard DNA and labeled sample DNA, gene mutation was detected as described for exon 4. The results are shown in Table 10. As shown in Table 10, the three gene types could be clearly distinguished.

TABLE 10

| Standard DNA solution (unlabeled) | Sample DNA solution (labeled) | Absorbance (A405) |
|---|---|---|
| Normal (pEX21N origin) | Normal (pEX21N) | 0.20 |
| Normal (pEX21N origin) | Mix of normal (pEX21N) and mutant (pEX21M) | 0.51 |
| Normal (pEX21N origin) | Mutant (pEX21M) | 1.16 |

EXAMPLE 5

In this method, a plasmid having a part of exon 10 tandemly ligated was prepared and the plasmid was excised with a restriction enzyme to form an unlabeled standard DNA. Gene mutation was detected using the unlabeled standard DNA. In this case, the sequence of the unlabeled standard DNA is not completely the same as that of the labeled DNA, and the unlabeled standard DNA had an additional sequence, $^5$CCT$^3$' at the 5'-terminal of each strand.

Unlabeled DNA  $^5$C C T___ AGG$^3$'
              $_3$GGA ___ TCC$_5$'

Labeled DNA       =

Preparation of unlabeled standard DNA and experiment using it

A mass production experiment of incorporating an unlabeled standard DNA into a plasmid using exon 10 was carried out.

(1) Preparation of pUC-Sfi/Stu 5 pmol of an oligonucleotide 5'-OH-GATCAGGCCTAAAAGGCCT (SEQ. ID. NO.21) and 5 pmol of an oligo-nucleotide 5'-OH-GATCAGGCCTTTTAGGCCT (SEQ. ID. NO.22) were annealed, and then, inserted into pCU119 (100 ng) that had been cleaved with BamHI, obtaining pUC-Sfi/Stu as represented by the following restriction enzyme map (1).

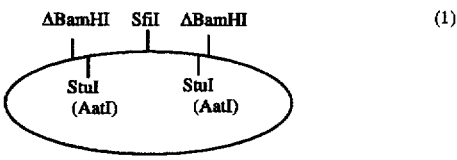

(2) Preparation of pUC-Sfi/Stu-EX10

PCR amplification was carried out by using CF-10-LigU (SEQ. ID. NO.23) (100 ng) and CF-10-LigL (SEQ. ID. NO.24) (100 ng) together with pEX10N (1 ng) as the template. The amplified product was cleaved with SfiI, and a fragment of about 190 bp was recovered by agarose gel electrophoresis. This fragment was inserted into the pUC-Sfi/Stu that had been cleaved with Sfi. With the base sequence confirmed, there was obtained pUC-Sfi/Stu-Ex10, which is represented by the following restriction enzyme map (2).

CF-10-LigU

5'OH-TTTAGGCCTAAAAGGCCTGATTAT
GGGAGAACTGGA                    (SEQ ID NO:23)

CF-10-LigL

5'OH-CCCAGGCCTTTTAGGCCTCTTCTA
GTTGGCATGCTT                    (SEQ ID NO:24)

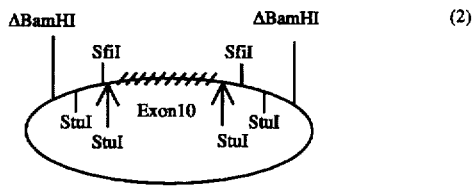

(3) Preparation of pUC-EX10Lig

300 μg of pUC-Sfi/Stu-EX10 was cleaved with SfiI, and a fragment of about 190 bp was refined by agarose gel electrophoresis. 2 μg of this fragment was ligated with 10 ng of pUC-Sfi/Stu that had been cleaved with SfiI, and E. coli DH5 was transformed therewith. A plasmid was produced from the transformant, obtaining pUC-EX10Lig containing about 15 tandemly ligated fragments containing exon 10 as represented by the following restriction enzyme map (3). This plasmid was cleaved with StuI (AatI) to excise a fragment containing exon 10.

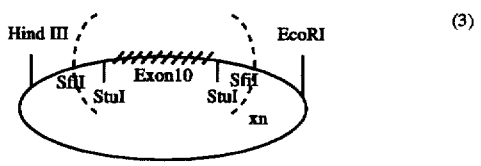

Detection of gene mutation using pUC-EX10Lig as unlabeled standard DNA

A labeled sample DNA was prepared by the PCR method using CF10P101-Bio (100 ng) and CF10M101-DNP (100 ng) together with a plasmid as described below as the template.

| Normal: | 1 ng of pEX10N |
|---|---|
| Mutation in one allele: | 0.5 ng of pEX10N |
| | 0.5 ng of pEX10M |
| Mutation in both alleles: | 1 ng of pEX10M |

An unlabeled standard DNA used the following (a) to (d).

(a) CF10P101-NH$_2$ (100 ng) and CF10M101-NH$_2$ (100 ng) and pEX10N (1 ng) as the template were used, prepared by the PCR method.
(b) pUC-EX10Lig cleaved with StuI (AatI) (see restriction enzyme map (3), above) was used without further purification.
(c) pUC-EX10Lig cleaved with StuI (AatI) (see restriction enzyme map (3), above) with further separation by agarose gel electrophoresis to purify a fragment containing exon 10.
(d) pUC-EX10Lig cleaved by EcoRI-HindIII (see restriction enzyme map (3), above)

Gene mutation was detected as in Example 4 using the unlabeled standard DNA and labeled sample DNA. The results are shown in Table 11.

TABLE 11

| Sample DNA solution | Preparation of standard DNA (unlabeled) | | | |
|---|---|---|---|---|
| (labeled) | a | b | c | d |
| Normal (pEX10N origin) | 0.07 | 0.14 | 0.15 | 0.84 |
| Mix of normal (pEX10N) and mutant (pEX10M) | 0.28 | 0.38 | 0.33 | 0.81 |
| Mutant (pEX10M) | 0.74 | 0.86 | 0.72 | 0.78 |

As shown in Table 11, the standard DNAs prepared by the methods of (b) and (c) gave results comparable to the results obtained by the method of (a) that had been prepared by the PCR method. On the other hand, substantially no competitive hybridization occurred in the case of (d), which remained tandemly ligated.

The above results indicate that an unlabeled standard DNA can be satisfactorily prepared from a plasmid containing tandemly ligated fragments using a restriction enzyme. The unlabeled standard DNA can be used without further purification. It is further seen that the unlabeled DNA having a sequence which is not completely identical with the labeled DNA and having an extra sequence on either terminal can also be satisfactorily used.

It has been confirmed by Examples 1 to 5 that the nucleic acid differentiating method of the present invention allows for direct and quick determination of the presence/absence of normal and mutant genes in a specimen as well as the ratio of mutant to normal genes. Therefore, the present invention makes possible the assays that have been difficult to accomplish by conventional methods, for example, such as detection of the presence/absence of a mutation at a non-specific site within a particular gene, detection of a small amount of abnormal cells containing a mutant gene in admixture with normal cells, and determination of sequence matching of a specific gene in a plurality of samples. The nucleic acid differentiating method of the present invention plays a great role in diagnosis of genetic diseases or in DNA diagnosis of cancer.

We claim:

1. A nucleic acid differentiating method for determining the presence, absence or quantity of a mutation or different allele in a particular nucleic acid sequence in a particular region of a target nucleic acid in a specimen, comprising the steps of:

preparing a labeled sample DNA by effecting gene amplification of the particular region of the target nucleic acid in the specimen by using target nucleic acid-amplifying primers comprising a primer having a detectable label introduced therein and a primer having a solid matrix-binding site introduced therein;

adding an excess molar amount of an unlabeled standard DNA to be evaluated for its matching with said labeled sample DNA to said labeled sample DNA;

effecting competitive hybridization between said labeled sample DNA and said unlabeled standard DNA; and binding said solid matrix-binding site to a solid matrix and measuring the amount of detectable label bound to said solid matrix to determine the amount of binding between said labeled sample DNA and DNA having a solid matrix binding site, thereby determining the presence, absence or quantity of said mutation or different allele.

2. The differentiating method according to claim 1, wherein said unlabeled standard DNA to be evaluated for its matching with the sample DNA has been prepared by a gene amplification technique using a pair of primers.

3. The differentiating method according to claim 1, wherein said unlabeled standard DNA to be evaluated for its matching with the sample DNA has been prepared by a genetic engineering technique using a vector which can propagate in a host cell.

4. The differentiating method according to any one of claims 1 to 3, wherein said particular region of a target nucleic acid in a specimen is a CFTR gene.

5. The differentiating method according to claim 1, wherein said label is a radioactive label.

6. The differentiating method according to claim 1, wherein said label is a non-radioactive label.

7. The differentiating method according to claim 1, wherein the difference in strand length between the labeled sample DNA and the unlabeled standard DNA is within 10 bases at each terminal end of the DNA's.

8. The differentiating method according to claim 1, which is performed to differentiate between alleles of a gene in a particular region of a target nucleic acid specimen.

9. The differentiating method according to claim 2, wherein said gene amplification technique is polymerase chain reaction.

* * * * *